(12) United States Patent
Cahan et al.

(10) Patent No.: US 10,360,501 B2
(45) Date of Patent: Jul. 23, 2019

(54) REAL-TIME CAPTURE AND TRANSLATION OF HUMAN THOUGHTS AND IDEAS INTO STRUCTURED PATTERNS

(71) Applicant: International Business Machines Corporation, Armonk, NY (US)

(72) Inventors: Amos Cahan, Dobbs Ferry, NY (US); Yishai Feldman, Tel Aviv (IL); Mohammad Sadoghi Hamedani, Chappaqua, NY (US); Padmanabhan Santhanam, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/985,867

(22) Filed: Dec. 31, 2015

(65) Prior Publication Data

US 2017/0193082 A1    Jul. 6, 2017

(51) Int. Cl.
| | |
|---|---|
| *G06N 5/00* | (2006.01) |
| *G06Q 10/10* | (2012.01) |
| *G16H 15/00* | (2018.01) |
| *G06Q 50/18* | (2012.01) |

(52) U.S. Cl.
CPC ............... *G06N 5/00* (2013.01); *G06Q 10/10* (2013.01); *G06Q 50/18* (2013.01); *G16H 15/00* (2018.01); *Y02A 90/26* (2018.01)

(58) Field of Classification Search
CPC ............................ G06N 5/00; G06F 17/30654
USPC ........................................................ 707/805
See application file for complete search history.

(56) References Cited

U.S. PATENT DOCUMENTS

| | | | |
|---|---|---|---|
| 5,960,384 A * | 9/1999 | Brash ................. | G06F 17/2705 704/10 |
| 7,730,085 B2 | 6/2010 | Hassan et al. | |
| 8,156,154 B2 | 4/2012 | Taranov et al. | |
| 8,335,753 B2 | 12/2012 | Rappaport et al. | |
| 8,407,253 B2 | 3/2013 | Ryu et al. | |
| 8,442,940 B1 * | 5/2013 | Faletti ................. | G06F 17/2785 704/9 |
| 8,666,922 B2 | 3/2014 | Hohimer et al. | |
| 8,671,103 B2 | 3/2014 | Wu et al. | |
| 8,751,218 B2 | 6/2014 | Dang et al. | |
| 8,799,286 B2 | 8/2014 | Cooper et al. | |
| 8,868,468 B2 | 10/2014 | Peng et al. | |
| 8,959,045 B2 | 2/2015 | Patten et al. | |
| 8,996,989 B2 | 3/2015 | Fox | |
| 9,104,779 B2 | 8/2015 | Hunt et al. | |

(Continued)

*Primary Examiner* — Syling Yen
(74) *Attorney, Agent, or Firm* — Cantor Colburn LLP; Rahan Uddin

(57) ABSTRACT

Examples of techniques for the real-time capture and translation of human thoughts and ideas into structured patterns are disclosed. In one example implementation according to aspects of the present disclosure, a computer-implemented method may include capturing, by a processing device, unstructured data. The method may also include extracting key terms from the unstructured data. Additionally, the method may include assigning an attribute to at least one of the key terms. The method may further include generating, by the processing device, a structured pattern based on the key terms and the attributes.

15 Claims, 12 Drawing Sheets

(56) References Cited

U.S. PATENT DOCUMENTS

| | | | |
|---|---|---|---|
| 2005/0021383 A1* | 1/2005 | Fliess | G06Q 10/06311 |
| | | | 705/7.14 |
| 2006/0206306 A1* | 9/2006 | Cao | G06F 17/2775 |
| | | | 704/4 |
| 2007/0214164 A1* | 9/2007 | MacLennan | G06F 17/30943 |
| 2012/0158668 A1* | 6/2012 | Tu | G06Q 10/101 |
| | | | 707/687 |
| 2013/0006610 A1* | 1/2013 | Quadracci | G06F 17/2775 |
| | | | 704/9 |
| 2013/0060764 A1 | 3/2013 | Voinea et al. | |
| 2013/0254199 A1 | 9/2013 | Surendran et al. | |
| 2014/0372481 A1 | 12/2014 | Faghihi Rezaei et al. | |
| 2015/0169734 A1 | 6/2015 | Jain et al. | |
| 2015/0178273 A1 | 6/2015 | Hakkani-Tur et al. | |
| 2015/0235135 A1 | 8/2015 | Shastri et al. | |

\* cited by examiner

John Doe
July 20, 2015 9:35pm

ADMISSION NOTES
A previously healthy 19 y.o male from Greensboro, NC, referred to the E.R by his primary care physician for suspected meningococcemia.

History: Two days prior to admission developed fever up to 102.5°F accompanied by chills, malaise, headache and mild dry cough. Also reports passing loose stools. On the day of admission, noticed a pink rash on his hands. Denies contact with sick people, travel or practicing unsafe sex. Denies vomiting. Does not recall having been bitten by a tick but enjoys jogging in the park and has occasional in contact with dogs. Does not use medications. His doctor has seen him, suspected meningococcemia and referred him to hospital.

OE: Temp 40.1°C, HR 115/min, BP 100/65mmHg, RR 22, SpO2 94% RA
Alert, coherent, mildly tachypneic, no nuchal rigidity, PERRLA, some conjuctival injection, no tenderness over the sinuses, throat- clear, heart- steady S1S2, lungs- fine crackles over both bases, no prolonged expiration, abdomen- normal peristaltic sounds, soft, non-tender, no hepatosplenomegaly, limbs- equal, no edema present, no enlargement of cervical, axillary or inguinal lymph nodes, skin- fine blanching papulo-macular rash over wrists and ankles, mild macular rash over chest.

*FIG. 4*

John Doe
July 20, 2015 9:35pm

ADMISSION NOTES
A previously healthy 19 y.o male from Greensboro, NC, referred to the E.R by his primary care physician for suspected meningococcemia.

History: Two days prior to admission developed fever up to 102.5°F accompanied by chills, malaise, headache and mild dry cough. Also reports passing loose stools. On the day of admission, noticed a pink rash on his hands. Denies contact with sick people, travel or practicing unsafe sex. Denies vomiting. Does not recall having been bitten by a tick but enjoys jogging in the park and has occasional in contact with dogs. Does not use medications. His doctor has seen him, suspected meningococcemia and referred him to hospital.

OE: Temp 40.1°C, HR 115/min, BP 100/65mmHg, RR 22, SpO2 94% RA
Alert, coherent, mildly tachypneic, no nuchal rigidity, PERRLA, some conjuctival injection, no tenderness over the sinuses, throat- clear, heart- steady S1S2, lungs- fine crackles over both bases, no prolonged expiration, abdomen- normal peristaltic sounds, soft, non-tender, no hepatosplenomegaly, limbs- equal, no edema present, no enlargement of cervical, axillary or inguinal lymph nodes, skin- fine blanching papulo-macular rash over wrists and ankles, mild macular rash over chest.

*FIG. 5*

REAL-TIME CAPTURE AND TRANSLATION OF HUMAN THOUGHTS AND IDEAS INTO STRUCTURED PATTERNS

BACKGROUND

The present disclosure relates generally to capturing and analyzing data and, more particularly, to techniques for the real-time capture and translation of human thoughts and ideas into structured patterns.

Analysis of structured data provides important insights in data-rich environments found in various domains such as healthcare, commerce, intelligence, and law enforcement, among others. Often, however, the most valuable information is found in the minds of professionals and experts in these fields or in the documentation that they produce.

Unstructured data containing expert notes reflecting a summary of their analysis, opinions, and judgments remain underutilized. Access to, and use of, this data is often limited by the suboptimal performance of natural language processing (NLP) systems and by privacy concerns. For example, NLP systems typically fail to capture higher level concepts in textual notes when similar reference notes are not available, such as in admission notes summarizing a patient-doctor interaction. In such cases, NLP can only extract tokens that can form together a "bag of words" without the ability to reconstruct a pattern conveying the main ideas in the text by semantically and temporally linking these tokens to form a pattern. Moreover, privacy concerns limit sharing of narrative text as there is no existing way to automatically assure that the text does not include private or protected information. Even products of NLP systems are still regarded as potentially including private information.

Yet for it to be possible to leverage the knowledge and wisdom contained in expert minds and narrative text at scale, the higher concepts need to be machine-interpretable and sharable in a timely manner. There is a need for techniques to enable real-time capture of concepts and ideas in the minds of experts and in narrative text they produce in a structured fashion that is easily sharable. Patterns detected within the data can further facilitate performing research tasks by enabling information condensation, visual representation of the data, and comparison of the logical or mental outline of events, concepts, and ideas.

SUMMARY

In accordance with aspects of the present disclosure, a computer-implemented method for the real-time capture and translation of human thoughts and ideas into structured patterns is provided. The method may include capturing, by a processing device, unstructured data. The method may also include extracting key terms from the unstructured data. Additionally, the method may include assigning an attribute to at least one of the key terms. The method may further include generating, by the processing device, a structured pattern based on the key terms and the attributes.

In accordance with additional aspects of the present disclosure, a system for the real-time capture and translation of human thoughts and ideas into structured patterns is provided. The system may include a processor in communication with one or more types of memory. The processor may be configured to capture unstructured data, extract key terms from the unstructured data, assign an attribute to at least one of the key terms, and generate a structured pattern based on the key terms and the attributes.

In accordance with yet additional aspects of the present disclosure, a computer program product for the real-time capture and translation of human thoughts and ideas into structured patterns is provided. The computer program product may include a non-transitory storage medium readable by a processing circuit and storing instructions for execution by the processing circuit for performing a method. The method may include capturing unstructured data, extracting key terms from the unstructured data, assigning an attribute to at least one of the key terms, and generating a structured pattern based on the key terms and the attributes.

BRIEF DESCRIPTION OF THE DRAWINGS

The subject matter which is regarded as the invention is particularly pointed out and distinctly claimed in the claims at the conclusion of the specification. The forgoing and other features, and advantages thereof, are apparent from the following detailed description taken in conjunction with the accompanying drawings in which:

FIG. 4 illustrates medical admission notes of an admitting physician according to examples of the present disclosure;

FIG. 5 illustrates the medical admission notes of FIG. 4 with key terms according to examples of the present disclosure;

DETAILED DESCRIPTION

Various implementations are described below by referring to several examples of the real-time capture and translation of human thoughts and ideas into structured patterns. The present disclosure describes uses of such structured patterns as part of expert knowledge networks, including knowledge sharing and analytics. The uses of the proposed system include at least decision support, education through feedback, and providing a spatiotemporal perspective of problems or issues encountered through multiple users across multiple locations. These and other advantages will be apparent from the description that follows.

Figure 1:
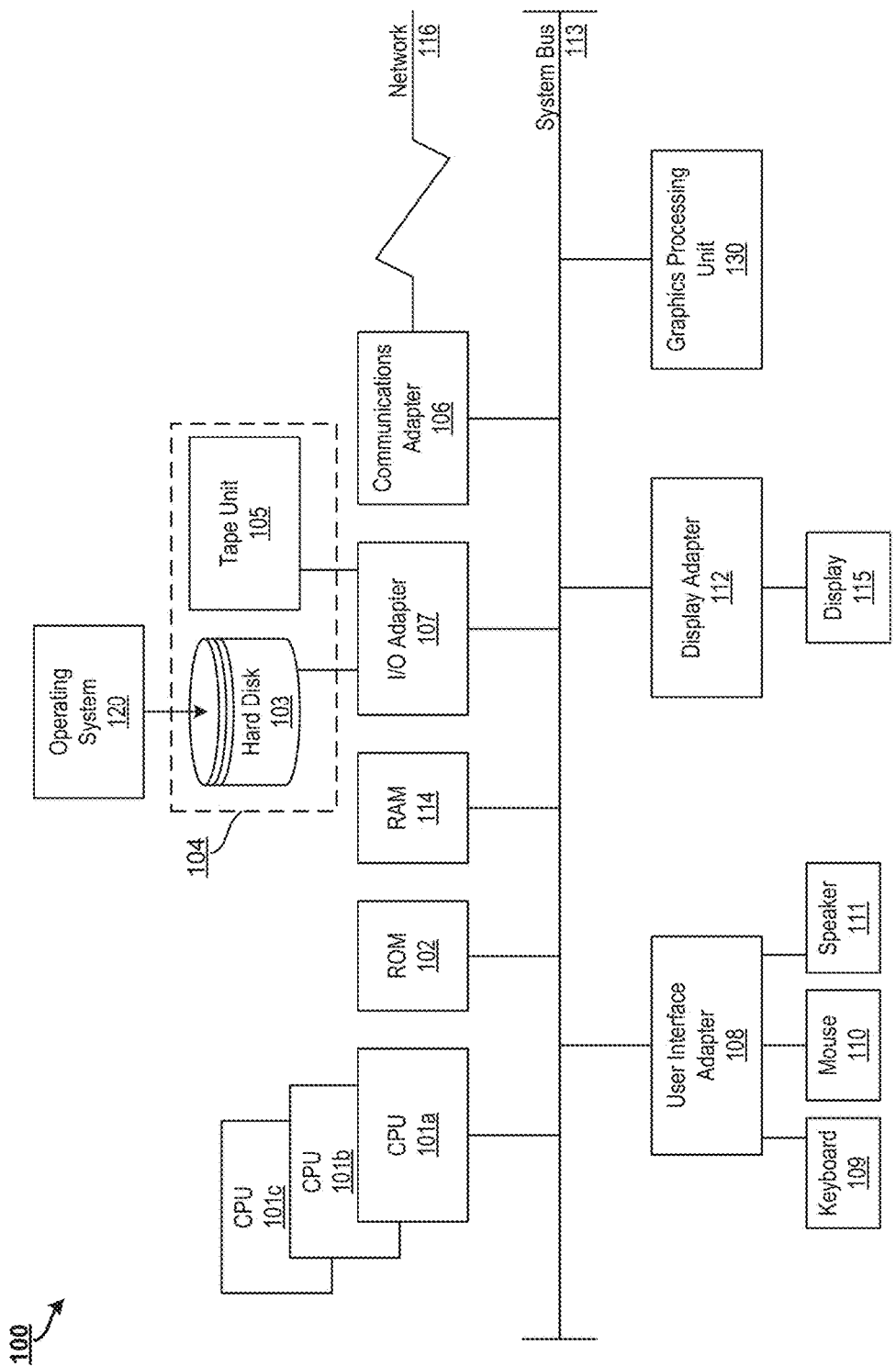
FIG. 1 illustrates a block diagram of a processing system for implementing the techniques described herein according to examples of the present disclosure.

FIG. 1 illustrates a block diagram of a processing system 100 for implementing the techniques described herein. In examples, the processing system 100 has one or more central processing units (processors) 101a, 101b, 101c, etc. (collectively or generically referred to as processor(s) 101). In aspects of the present disclosure, each processor 101 may include a reduced instruction set computer (RISC) microprocessor. Processors 101 are coupled to system memory (e.g., random access memory (RAM) 114 and various other components via a system bus 113. Read only memory (ROM) 102 is coupled to the system bus 113 and may include a basic input/output system (BIOS), which controls certain basic functions of the processing system 100.

FIG. 1 further illustrates an input/output (I/O) adapter 107 and a communications adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling the processing system 100 to communicate with other such systems.

A screen (e.g., a display monitor) 115 is connected to system bus 113 by display adaptor 112, which may include a graphics adapter to improve the performance of graphics intensive applications and a video controller. In one aspect of the present disclosure, adapters 106, 107, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

In some aspects of the present disclosure, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 1, the processing system 100 includes processing capability in the form of processors 101, storage capability including system memory 114 and mass storage 104, input means such as keyboard 109 and mouse 110, and output capability including speaker 111 and display 115. In some aspects of the present disclosure, a portion of system memory 114 and mass storage 104 collectively store an operating system such as the AIX® operating system from IBM Corporation to coordinate the functions of the various components shown in FIG. 1.

Figure 2:
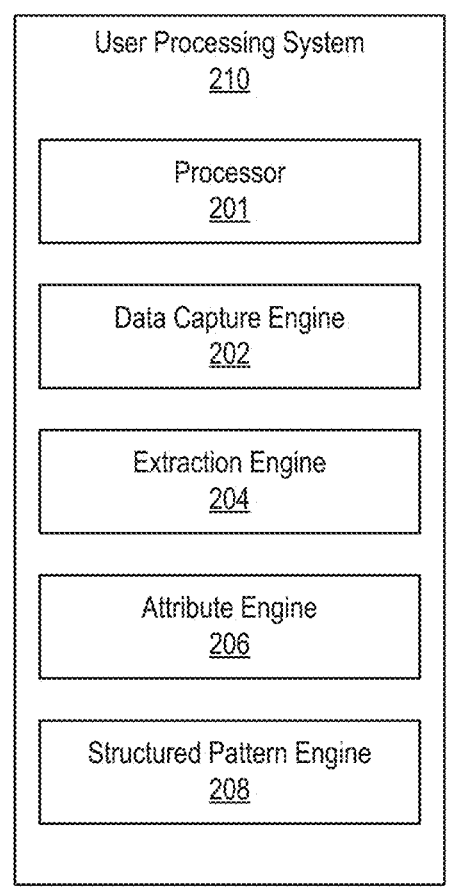
FIG. 2 illustrates a block diagram of a processing system for the real-time capture and translation of human thoughts and ideas into structured patterns according to examples of the present disclosure.

FIG. 2 illustrates a block diagram of a processing system 200 for the real-time capture and translation of human thoughts and ideas into structured patterns according to examples of the present disclosure. The various components, modules, engines, etc. described regarding FIG. 2 may be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these. In examples, the engine(s) described herein may be a combination of hardware and programming. The programming may be processor executable instructions stored on a tangible memory, and the hardware may include processing device 201 for executing those instructions. Thus system memory 114 of FIG. 1 can be said to store program instructions that when executed by processing device 201 implement the engines described herein. Other engines may also be utilized to include other features and functionality described in other examples herein.

Processing system 200 may include processing device 201, data capture engine 202, extraction engine 204, attribute engine 206, and structured pattern engine 208. Alternatively or additionally, the processing system 200 may include dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein.

Data capture engine 202 captures unstructured data, for example, from a user. The unstructured data may represent thoughts, arguments, concepts, images, analysis, frameworks, inter-related pieces of information, etc., generated in the mind of a human user or found in an external source (e.g., person, event, website, book, article, photograph, video, art piece, etc.). The admissions notes illustrated in FIG. 4 represent one example of unstructured data.

Extraction engine 204 extracts key terms from the unstructured data. The key terms may be extracted by applying a natural language processing (NLP) techniques to the unstructured data, for example. In other examples, the user may be presented with the unstructured data to enable the user to indicate the key terms. FIG. 5 illustrates examples of key terms that are extracted, for example, by an NLP technique or by a user.

Figure 6:
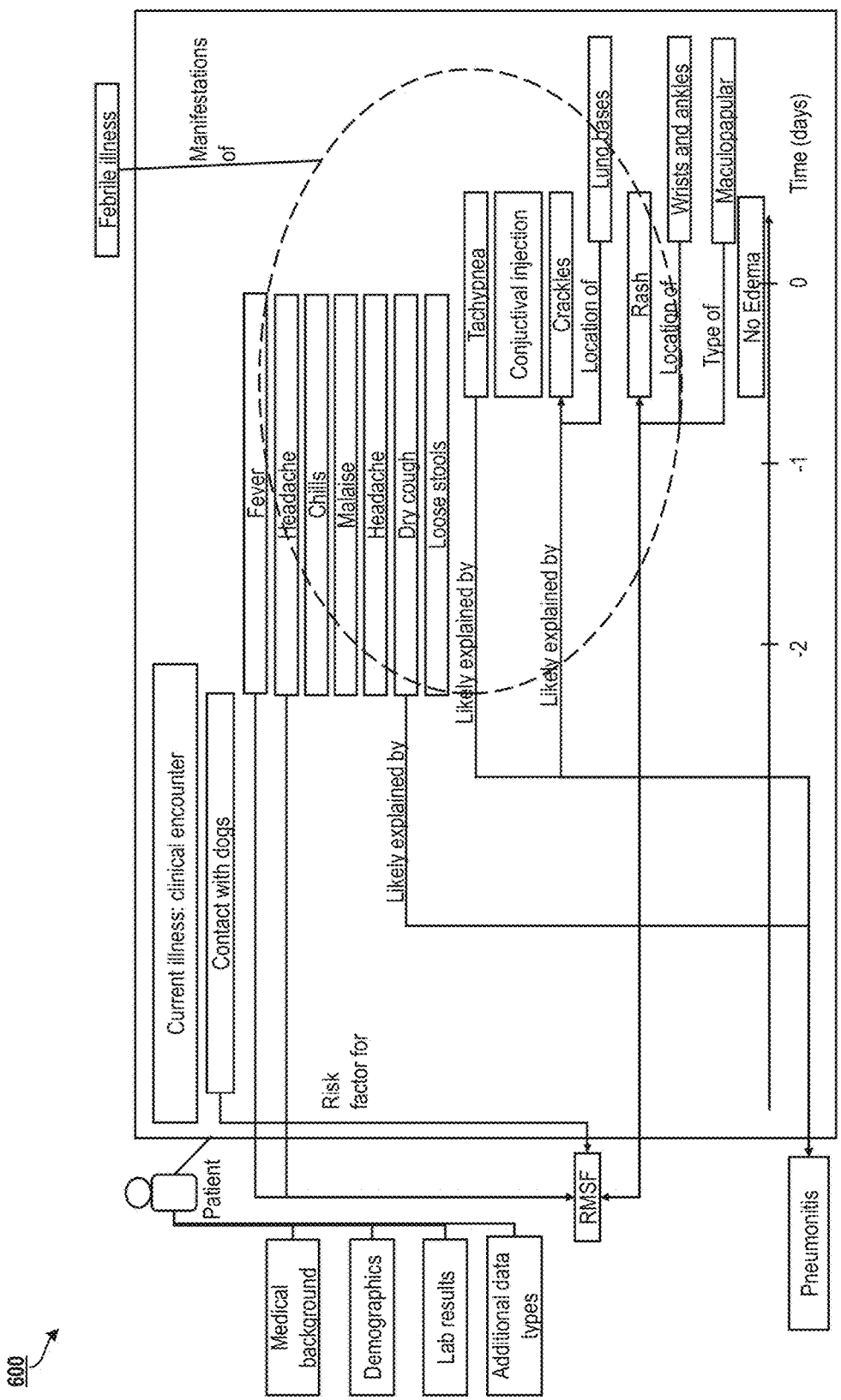
FIG. 6 illustrates a structured pattern generated based on the key terms of FIG. 5 according to examples of the present disclosure.

Attribute engine 206 assigns an attribute to at least one of the key terms. For example, the user may be presented with the key terms. The user may then assign an attribute (or multiple attributes) to one or more of the key terms. Examples of attributes may include at least the following: temporal order, similarity, cause and effect relationships, areas of doubt or missing pieces of evidence, conditions, meta-data, hypothetic links, suspicions, degree of confidence, information source, contradictions between components, and the like. The structured pattern illustrated FIG. 6 shows examples attributes in the context of a patent illness clinical encounter.

Structured pattern engine 208 generates a structured pattern based on the key terms and the attributes. An example of a structured pattern is illustrated in FIG. 6.

Processing system 200 may be implemented to perform the techniques described herein in a variety of different scenarios, including in the medical, legal, research, finance, and sports fields. In the medical field, the present techniques may generate a structured pattern describing the components of a disease presentation or a patient's course. For a given patient, the medical background information, symptoms as elicited by an interviewing healthcare professional (or provided directly by the patient), findings in physical examination, laboratory results, imaging findings, and the like can be collected as unstructured data. These components (i.e., key terms) can be inter-related through attributes in their sequence of occurrence, evolvement over time, in some components being a cause or consequence of others, in some components being more important than others, in some components being contradictory to others, etc. Generation of a structured pattern reflecting at least some of the attributes between components in real time enables the structured pattern to be compared to other patterns (e.g., patterns created for other patients or to disease descriptions in medical literature). If patterns are associated with diagnoses, then by this process a diagnosis could be suggested for the patient. Using patterns can serve as an educational tool for teaching the art of interacting with patients and making diagnoses for example. Patterned structured data created through interaction with a care provider can be assumed not to contain personal information and is therefore sharable in real-time.

In the legal field, investigators and/or attorneys may use structured patterns to link pieces of evidence related to one another in context of a crime, a suspect, a group of people, etc. Structured patterns can be used to present a concise picture of events and/or ideas and can be compared to other structured patterns, enabling the investigators and/or attorneys to learn from the experience of others. In examples, a judge can form structured patterns reflecting the sequence of events in a case or the arguments made by the defense and prosecution in order to detect precedence, highlight points of agreement and contradiction, link evidence to claims, etc.

In the research field, a scientist can create a structured pattern to reflect a theory, inter-relate findings in various experiments, compare possible explanations for a set of observations, summarize claims and supporting evidence made in a journal article, etc. In examples, a journalist may use a structured pattern to display pieces of information gathered for an article (e.g., a review) and use the structured pattern to highlight missing parts that need further investigation, or compare the structured pattern to other structured patterns in a database, enabling the journalist to retrieve similar stories or reports.

Similarly, structured patterns can be useful in the financial domains to represent relations between players in an industry, areas of uncertainty, cause and effect speculations and market predictions towards the future, etc. Comparison to structured patterns may be used to detect similarities and important differences between business cases, compare with historic events, and support predictions.

In sports, coaches may analyze sequences of events in a game to reveal the behavior of a rival player or the strategy of another team. The coach could use patterns to form and present his own strategies. Analysts could use patterns to represent their observations and theories, thereby improving prediction of future behaviors and game results.

Figure 3:
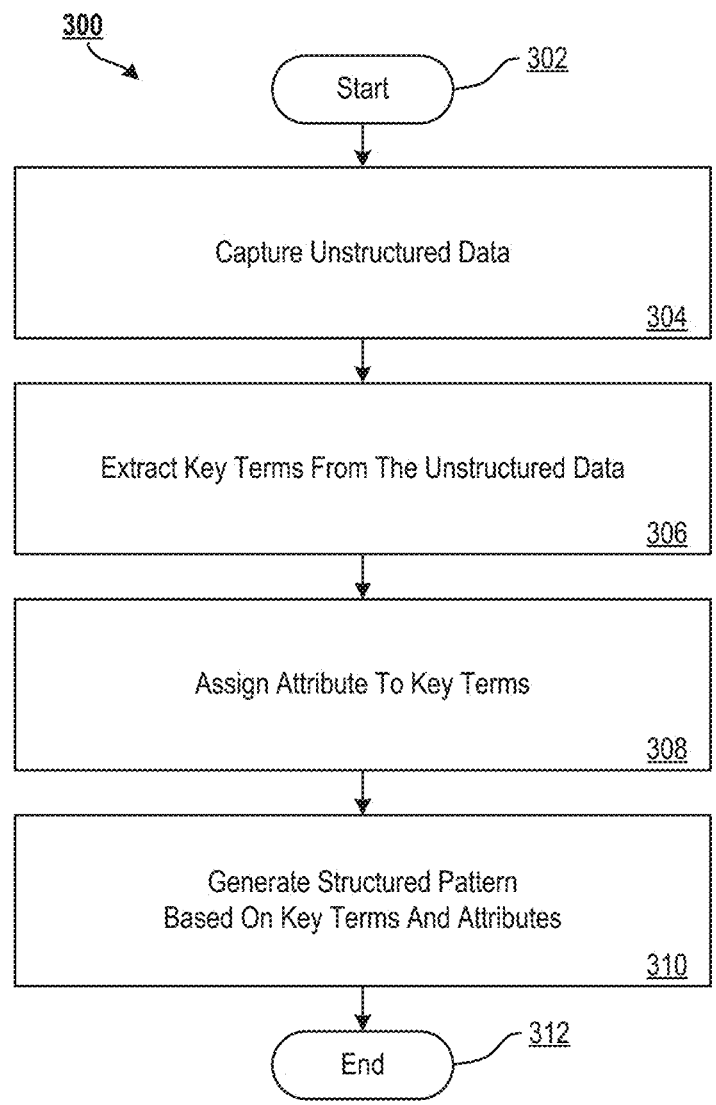
FIG. 3 illustrates a flow diagram of a method for the real-time capture and translation of human thoughts and ideas into structured patterns according to examples of the present disclosure.

FIG. 3 illustrates a flow diagram of a method 300 for the real-time capture and translation of human thoughts and ideas into structured patterns according to examples of the present disclosure. Method 300 starts at block 302 and continues to block 304.

At block 304, method 300 includes a processing device (e.g., processing system 200 of FIG. 2) capturing unstructured data. The unstructured data may represent human thoughts and ideas. In examples, the unstructured data is captured via a user interface that is presented to a user. The user may enter the data directly in some examples, while in other examples the unstructured data is captured as a background process while the user is entering data into another program. The unstructured data may also be captured via voice recognition.

At block 306, method 300 includes extracting key terms from the unstructured data. Extracting the key terms may include presenting the unstructured data to the user and enabling the user to select or indicate the key terms. In other examples, extracting the key terms is performed using a natural language processing (NPL) technique. This enables the key terms to be extracted in real time. In examples, the unstructured data captured at block 304 include a plurality of terms, and the key terms are a subset of the plurality of terms.

At block 308, method 300 includes assigning an attribute to at least one of the key terms. Examples of attributes may include at least the following: temporal order, similarity, cause and effect relationships, areas of doubt or missing pieces of evidence, conditions, meta-data, hypothetic links, suspicions, degree of confidence, information source, contradictions between components, and the like. In examples, assigning the attribute to at least one of the key terms further comprises presenting the key terms to a user to enable the user to assign the attribute to the at least one of the key terms.

At block 310, method 300 includes the processing device generating a structured pattern based on the key terms and the attributes. An example of a structured pattern is illustrated in FIG. 6 and described below. Method 300 continues to block 312 and terminates.

Additional processes also may be included. For example, method 300 may include comparing, by the processing device, the structured pattern with at least one existing structured pattern. This enables general/global interferences to be drawn based on a body of analyzed data. For example, comparing structured patterns enables classifying them, relating them to one another, finding similarities and differences between them, and using them to form more general patterns. In examples, method 300 may also include gathering relevant data from additional resources such as summary statistics to put structured patterns in context. Comparing structured patterns also enables summarizing relevant context data, generating similarity scores for a certain structured pattern feature compared to other structured patterns, advice and other decision support tools, educational tools such as system feedback on the user performance, spaciotemporal mapping of structured patterns and their evolvement, suggestions for additional components that could fit in a structure data pattern, and the like.

In additional examples, method 300 may also include presenting the structured pattern to a user graphically, such as presenting the structured pattern illustrated in FIG. 6. It should be understood that the processes depicted in FIG. 3 represent illustrations, and that other processes may be added or existing processes may be removed, modified, or rearranged without departing from the scope and spirit of the present disclosure.

FIG. 4 illustrates medical admission notes 400 of an admitting physician according to examples of the present disclosure. In particular, medical admission notes 400 provide unstructured data in the form of a simulated patient ("John Doe") with admission notes supplied by an admitting physician.

FIG. 5 illustrates the medical admission notes 400 of FIG. 4 with key terms according to examples of the present disclosure. In particular, medical admission notes 400 are illustrated with key terms being underlined. The key terms may be recognized through an NLP process and/or by the physician or other appropriate user.

FIG. 6 illustrates a structured pattern 600 generated based on the key terms of FIG. 5 according to examples of the present disclosure. In particular, structured pattern 600 provides a structured pattern for the patient ("John Doe") generated from the patient's medical admission notes 400 using the key terms identified in FIG. 5. The physician knowledge is represented by the graph on the right entitled "current illness: clinical encounter." Other structured data are automatically extracted and can be linked/added to the structured pattern. In the present example, an added layer of higher cognitive concepts is illustrated on top of the key terms. This layer represents hypothesis representing doubt (with optional addition of more information such as degree of confidence). Also, terms can be negated such as in "no edema." In this case, temporal inter-relations are represented by the term position on a time scale, but lines or other symbols (e.g., colors, shading, size, etc.) can be used to convey this information. When time frames are unknown, this may be represented by other indicia, such as a fading color.

Figure 7:
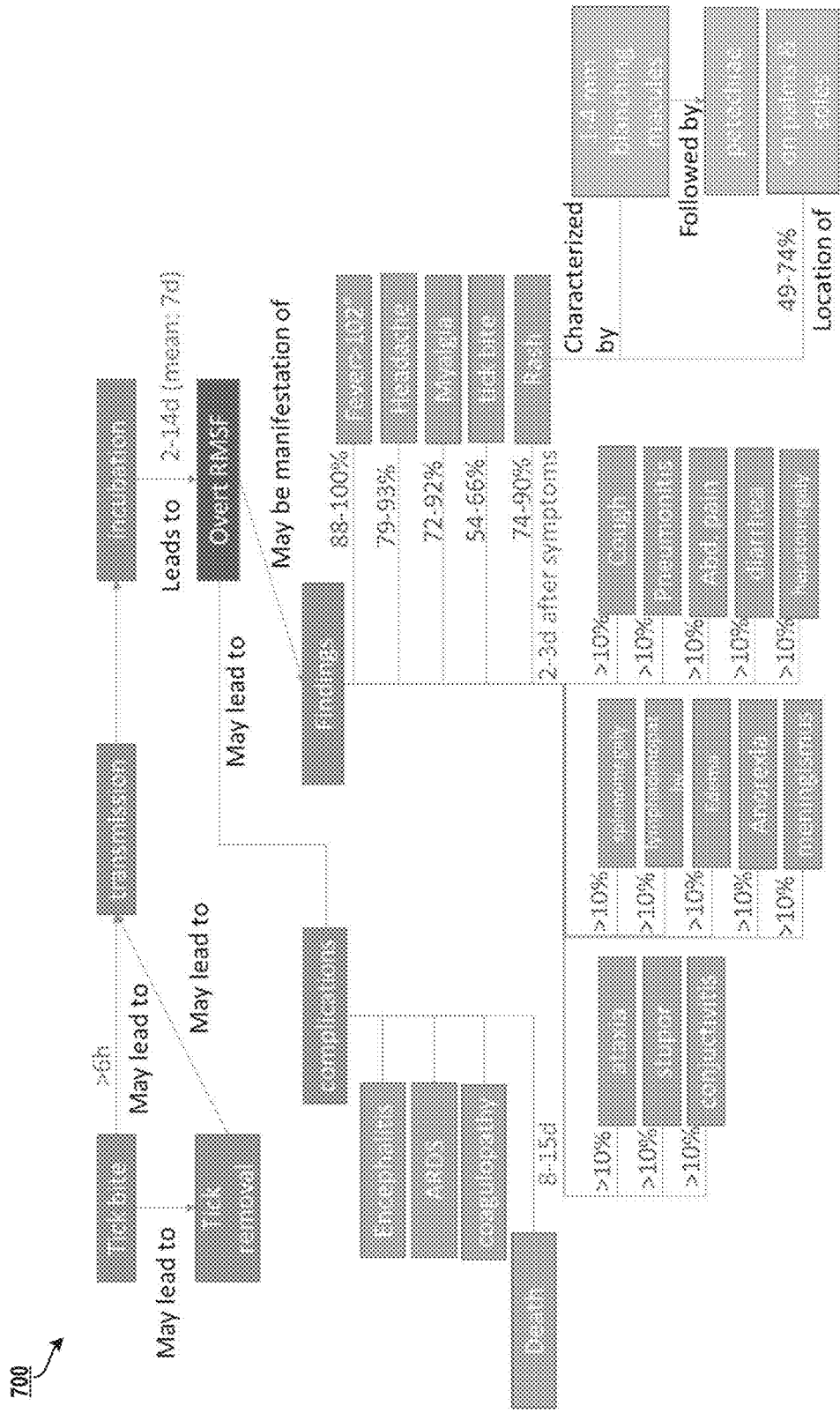
FIG. 7 illustrates a global structured pattern of a disease constructed by a physician based on textbook knowledge according to examples of the present disclosure.

FIG. 7 illustrates a global structured pattern 700 of a disease constructed by a physician based on textbook knowledge according to examples of the present disclosure. In this case, the disease is Rocky Mountain Spotted Fever (RMSF).

Figure 8A:
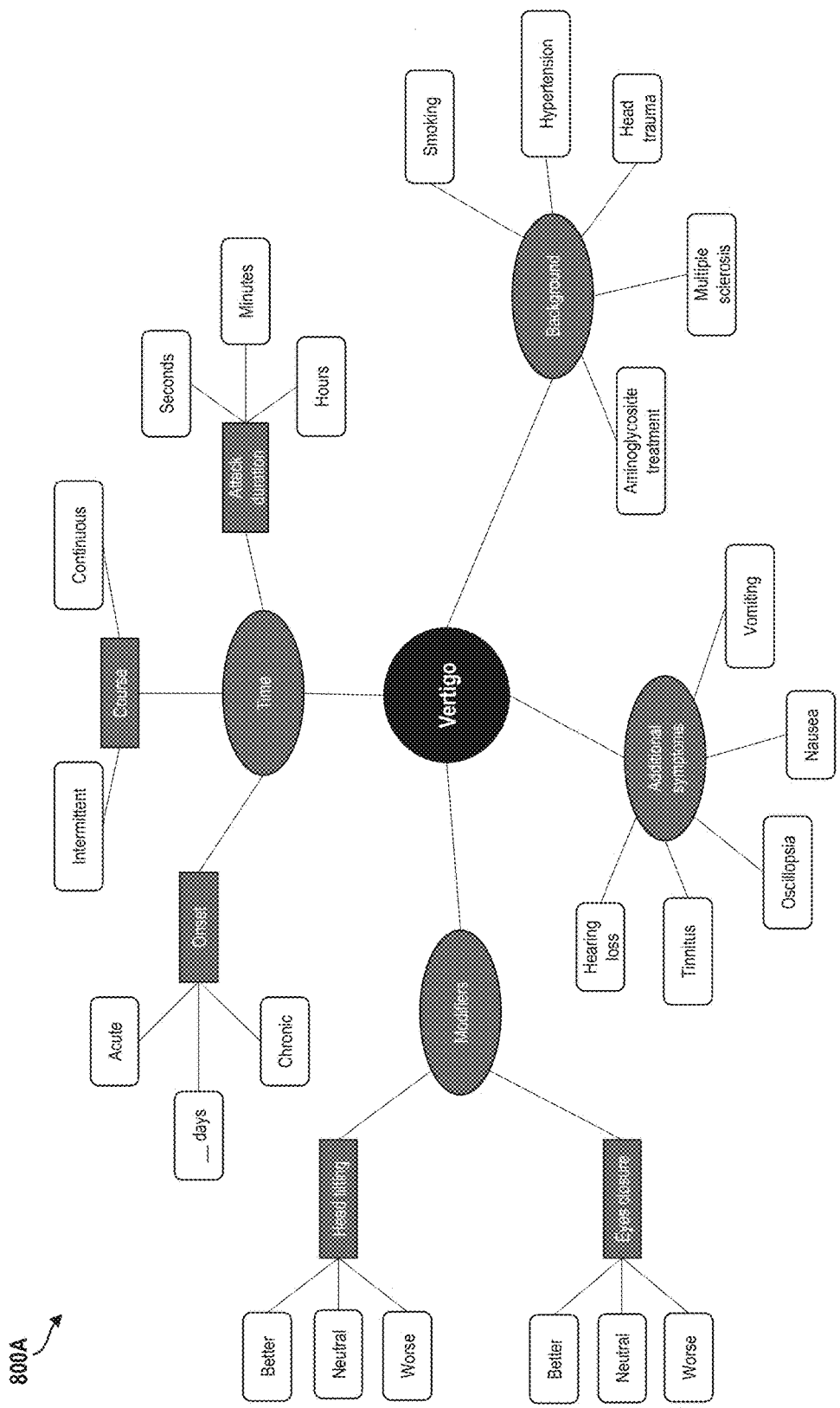
FIGS. 8A, 8B, and 8C illustrate a graphic view of structured patterns of possible characteristics of a disease according to examples of the present disclosure.
Figure 8B:
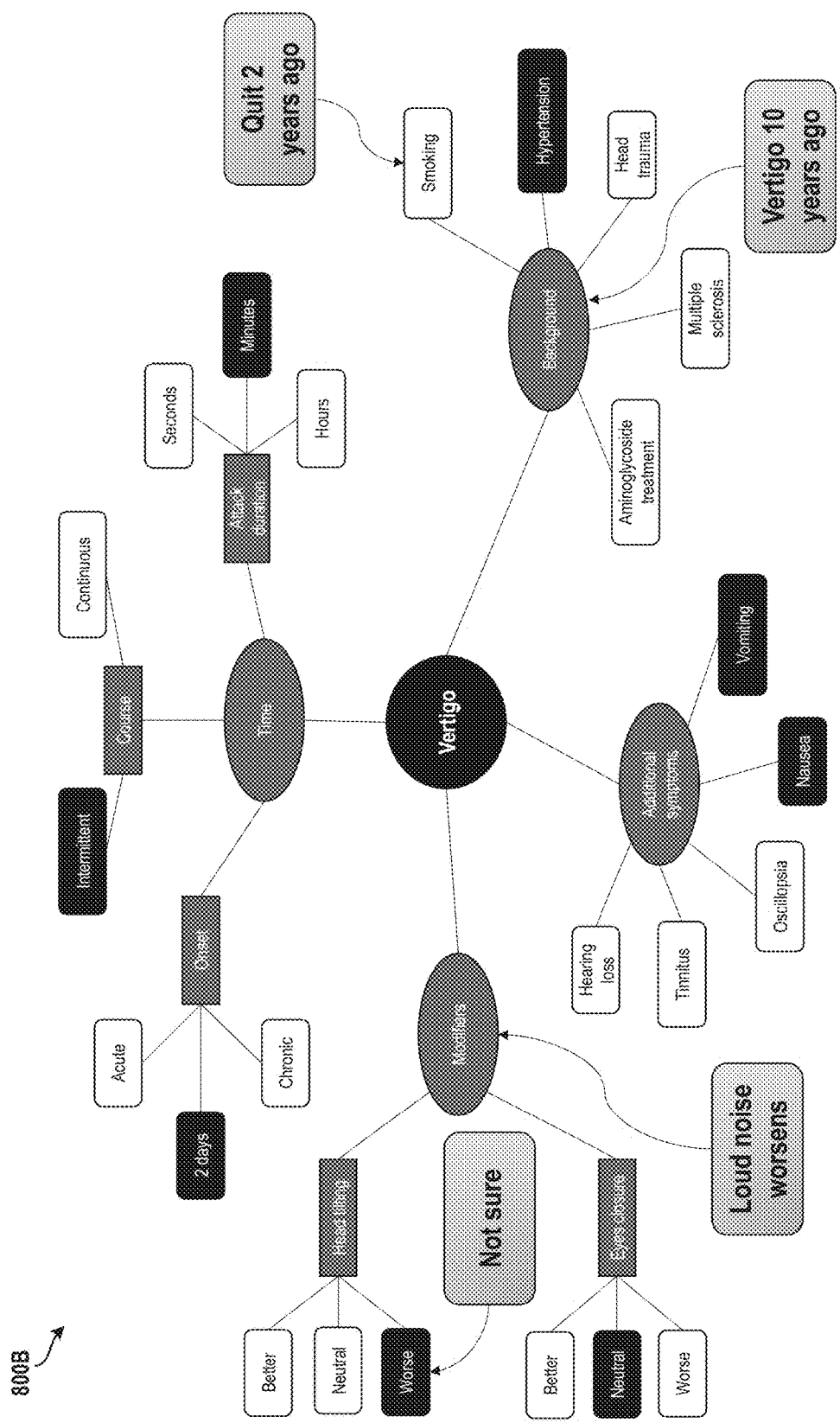
Figure 8C:
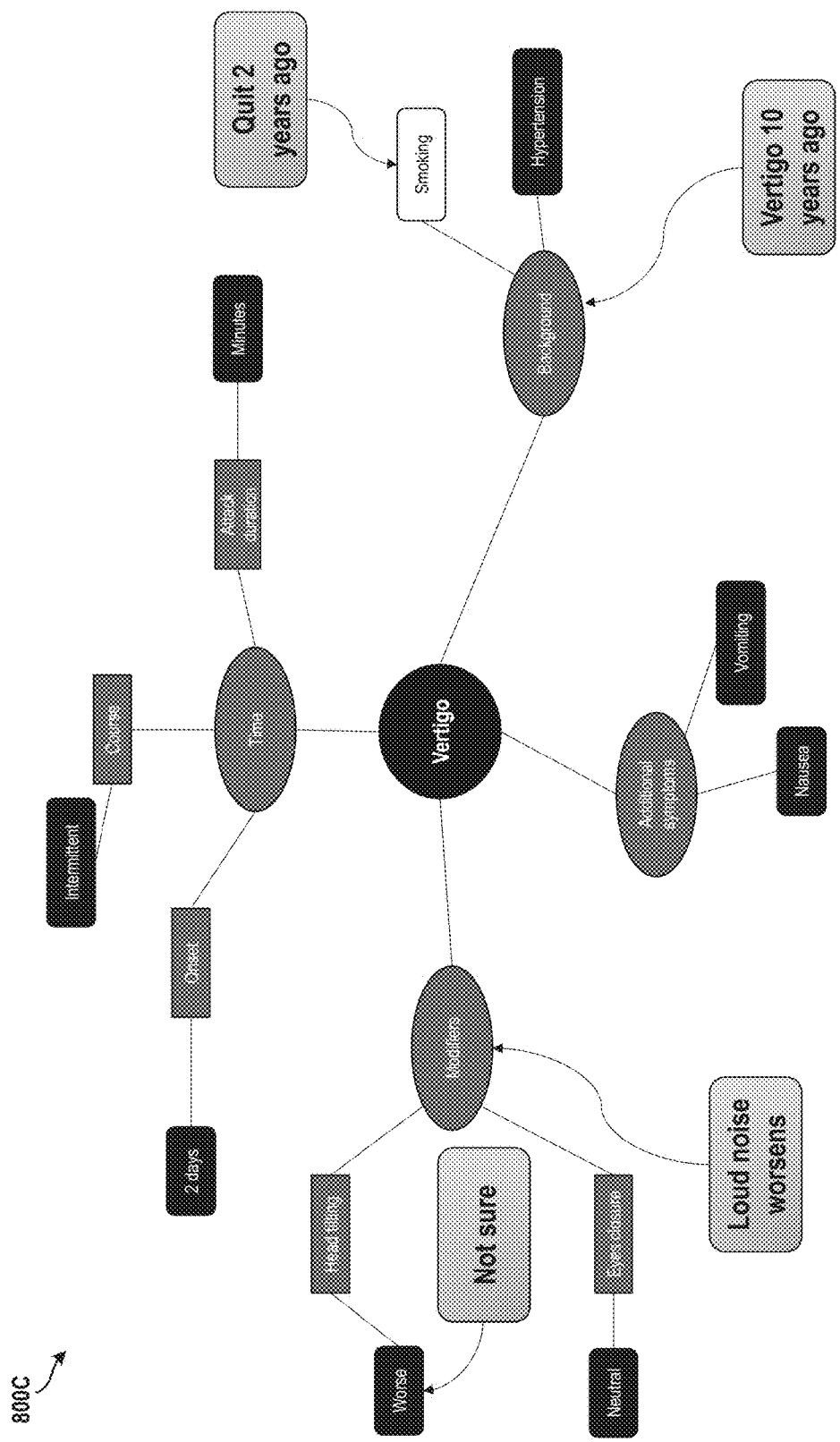

FIGS. 8A, 8B, and 8C illustrate a graphic view of structured patterns 800A, 800B, and 800C respectively of possible characteristics of a disease according to examples of the present disclosure. In particular, FIG. 8A illustrates another example of a graphic structured representation 800A of possible characteristics of a symptom (vertigo). FIG. 8B illustrates a structured pattern 800B generated by a physician by checking the features of vertigo in a specific patient. In examples, additional information may be added to the pattern by the user. In the example of FIG. 8B, a modifying factor "loud noise worsens" is added, along with time since smoking cessation ("Quit 2 years ago") and doubt ("not sure"). This information may be added in the form of free text and standardized using a NLP engine or entered in a standardized, structured form (e.g., using a drop-down menu). In this example, the term "vertigo" may be extracted from free text in an admissions note or selected by a physician through a "symptom/disease pattern search engine" to provide support while accessing a patent with vertigo. In this case, a generic pattern is displayed and modified or customized to fit a specific patient. FIG. 8C illustrates a personalized structured pattern 800C.

It is understood in advance that the present disclosure is capable of being implemented in conjunction with any other type of computing environment now known or later developed. In examples, the present disclosure may be implemented on cloud computing.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 9:
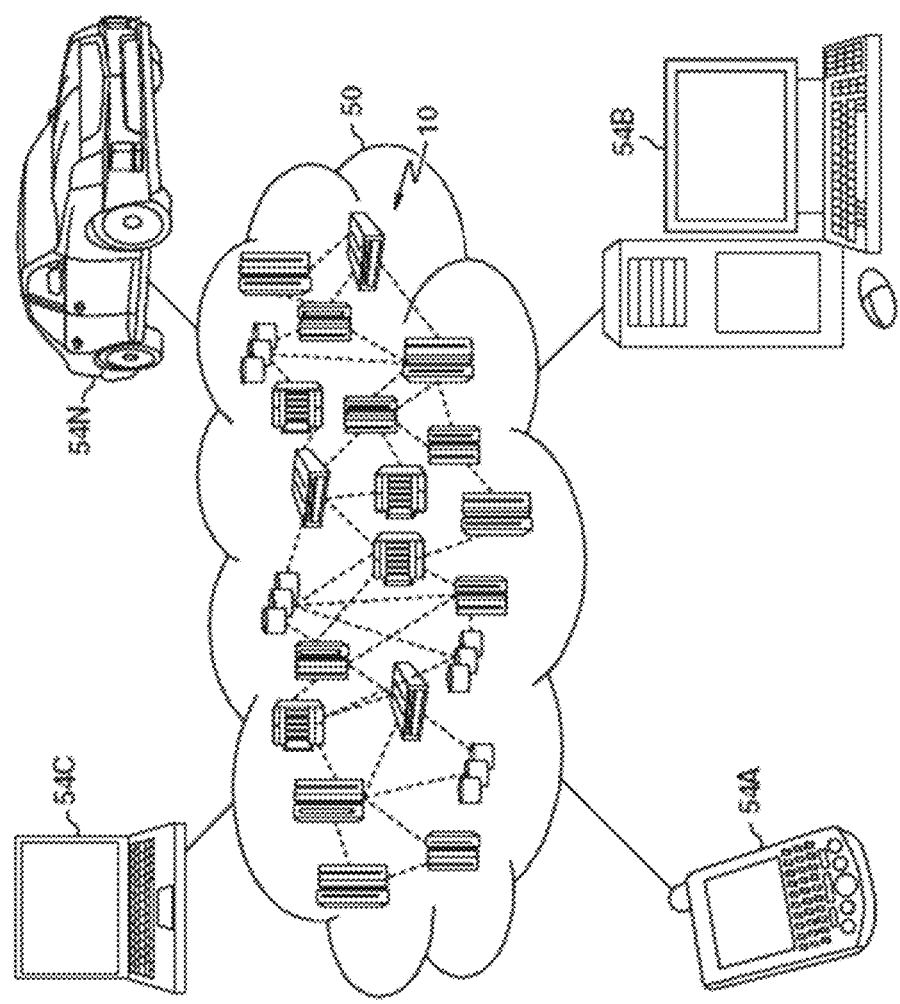
FIG. 9 illustrates a cloud computing environment according to examples of the present disclosure.

Referring now to FIG. 9, illustrative cloud computing environment 50 is illustrated. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 10 and cloud computing environment 50 can communicate with any type of computerized device over any type of network and/or network addressable connection (e.g., using a web browser).

Figure 10:
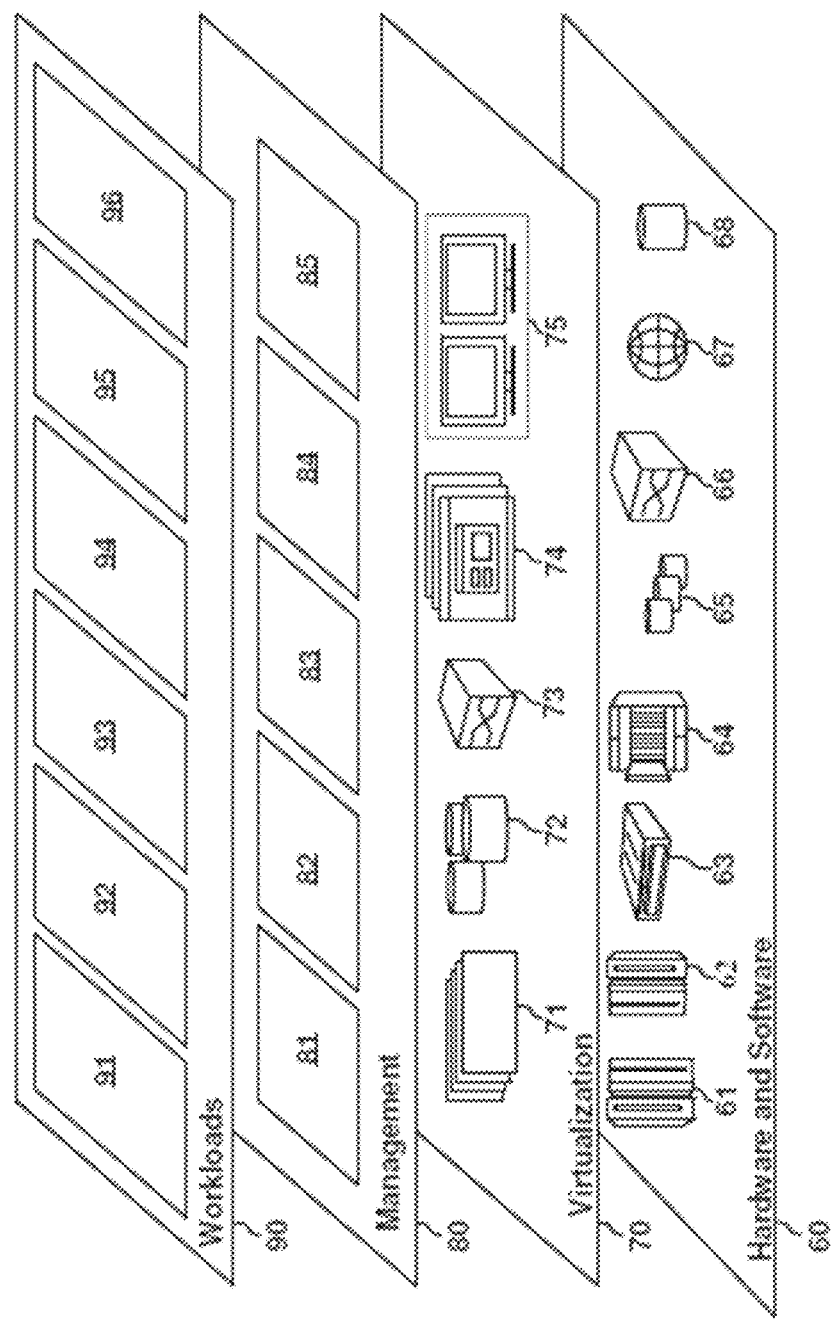
FIG. 10 illustrates abstraction model layers according to examples of the present disclosure.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As illustrated, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and real-time capture and translation of human thoughts and ideas into structured patterns 96.

The present techniques may be implemented as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some examples, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to aspects of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for real-time capture and translation of human thoughts and ideas into structured patterns, the method comprising:
    capturing, by a processing device, unstructured data, wherein the unstructured data represents human thoughts and ideas;
    extracting key terms from the unstructured data, wherein extracting the key terms from the unstructured data further comprises presenting the unstructured data to a user to enable the user to select the key terms from the unstructured data;
    assigning an attribute to at least one of the key terms selected by the user, wherein assigning the attribute further comprises assigning a plurality of attributes to the at least one of the key terms selected by the user, where the plurality of attributes comprises a temporal order, a similarity, a cause and effect relationship, an area of doubt, a condition, metadata, a hypothetic link, a suspicion, a degree of confidence, an information source, and a contradiction between components;
    generating, by the processing device, a structured pattern based on the key terms selected by the user and the attributes, wherein the structured pattern is a visual representation of the human thoughts and ideas represented by the unstructured data; and
    comparing, by the processing device, the structured pattern with at least one existing structured pattern.

2. The computer-implemented method of claim 1, wherein extracting the key terms from the unstructured data further comprises applying a natural language processing technique to the unstructured data.

3. The computer-implemented method of claim 1, wherein assigning the attribute to at least one of the key terms further comprises presenting the key terms to a user to enable the user to assign the attribute to the at least one of the key terms.

4. The computer-implemented method of claim 1, wherein the unstructured data comprises a plurality of terms, and wherein the key terms are a subset of the plurality of terms.

5. The computer-implemented method of claim 1, wherein capturing the unstructured data occurs via a user interface presented to a user.

6. The computer-implemented method of claim 1, further comprising:
    presenting the structured pattern to a user graphically.

7. The computer-implemented method of claim 1, wherein comparing the structured pattern further comprises generating a similarity score for a structured pattern feature of the structured pattern and the at least one existing structured pattern.

8. A system for the real-time capture and translation of human thoughts and ideas into structured patterns, the system comprising:
    a processor in communication with one or more types of memory, the processor configured to:
        capture unstructured data, wherein the unstructured data represents human thoughts and ideas;
        extract key terms from the unstructured data, wherein extracting the key terms from the unstructured data further comprises presenting the unstructured data to a user to enable the user to select the key terms from the unstructured data;
        assign an attribute to at least one of the key terms selected by the user, wherein assigning the attribute further comprises assigning a plurality of attributes to the at least one of the key terms selected by the user, where the plurality of attributes comprises a temporal order, a similarity, a cause and effect relationship, an area of doubt, a condition, metadata, a hypothetic link, a suspicion, a degree of confidence, an information source, and a contradiction between components;

generate a structured pattern based on the key terms selected by the user and the attributes, wherein the structured pattern is a visual representation of the human thoughts and ideas represented by the unstructured data; and compare the structured pattern with at least one existing structured pattern.

9. The system of claim 8, wherein extracting the key terms from the unstructured data further comprises applying a natural language processing technique to the unstructured data.

10. The system of claim 8, wherein assigning the attribute to at least one of the key terms further comprises presenting the key terms to a user to enable the user to assign the attribute to the at least one of the key terms.

11. The system of claim 8, wherein the unstructured data comprises a plurality of terms, and wherein the key terms are a subset of the plurality of terms.

12. The system of claim 8, wherein capturing the unstructured data occurs via a user interface presented to a user.

13. The system of claim 8, wherein the processor is further configured to:

present the structured pattern to a user graphically.

14. A computer program product for the real-time capture and translation of human thoughts and ideas into structured patterns, the computer program product comprising:

a non-transitory storage medium readable by a processing circuit and storing instructions for execution by the processing circuit for performing a method comprising:

capturing unstructured data, wherein the unstructured data represents human thoughts and ideas;

extracting key terms from the unstructured data, wherein extracting the key terms from the unstructured data further comprises presenting the unstructured data to a user to enable the user to select the key terms from the unstructured data;

assigning an attribute to at least one of the key terms selected by the user, wherein assigning the attribute further comprises assigning a plurality of attributes to the at least one of the key terms selected by the user, where the plurality of attributes comprises a temporal order, a similarity, a cause and effect relationship, an area of doubt, a condition, metadata, a hypothetic link, a suspicion, a degree of confidence, an information source, and a contradiction between components;

generating a structured pattern based on the key terms selected by the user and the attributes, wherein the structured pattern is a visual representation of the human thoughts and ideas represented by the unstructured data;

comparing the structured pattern with at least one existing structured pattern; and forming, by the processing device, a general pattern based on comparing the structured pattern with the at least one existing structured pattern.

15. The computer program product of claim 14, wherein extracting the key terms from the unstructured data further comprises applying a natural language processing technique to the unstructured data.

\* \* \* \* \*